United States Patent [19]

Ecke, Jr.

[11] Plant 4,951

[45] Nov. 16, 1982

[54] POINSETTIA NAMED WHITE CURLY

[75] Inventor: Paul Ecke, Jr., Encinitas, Calif.

[73] Assignee: Paul Ecke Ranch, Encinitas, Calif.

[21] Appl. No.: 255,820

[22] Filed: Apr. 20, 1981

[51] Int. Cl.[3] ..... A01H 5/00

[52] U.S. Cl. ..... Plt./86

[58] Field of Search ..... Plt./86

*Primary Examiner*—Robert E. Bagwill

*Attorney, Agent, or Firm*—Chas W. Rummler

[57] ABSTRACT

A new variety of poinsettia plant of the "curly" type distinguished by the shape of its leaves and bracts, the yellowish white color of the bracts, and by its vigorous growth habit with little tendency to branch.

2 Drawing Figures

BACKGROUND OF THE NEW PLANT

This new curly poinsettia was produced at my breeding facilities at Encinitas, Calif., as a hybrid resulting from many crossings of various seedlings or mutations including, in particular, Ecke's Flaming Sphere (U.S. Plant Pat. No. 1,052) which, because of its leaf shape, is responsible for the uniqueness of this new cultivar. This particular plant was selected from many white curly seedlings of similar but different types and was chosen by me as the best white of the many.

Reproduction of this plant was done under my direction at Encinitas, Calif., by means of cuttings, and successive generations of propagation of this plant have shown its novel characteristics to be fixed and to hold true from generation to generation.

DESCRIPTION OF THE DRAWINGS

My new poinsettia cultivar is illustrated by the accompanying full color photographic drawing, in which the upper view shows a potted plant in side elevation and the lower view shows the full face of each of a pair of heads in full bloom.

DESCRIPTION OF THE NEW PLANT

The following is a detailed description of this new variety of poinsettia plant, the color designations being stated according to The R.H.S. Colour Chart published by The Royal Horticultural Society of London, England.

THE PLANT

Origin: Hybrid seedling.

Parentage: Unknown.

Classification:

*Botanic.*—*Euphorbia pulcherrima.*

*Commercial.*—Curly poinsettia.

Form: Shrub.

Height: Medium.

Growth habit: Vigorous, upright and with moderately stiff stems which have little tendency to branch. After a stem is pinched back, only two or three branches will form.

Growth rate: Normal for poinsettias. Cuttings from this plant produce roots under greenhouse conditions similar to other poinsettias.

Foliage: Abundant.

*Leaf shape.*—The leaves and bracts are puckered and have an arching or curly effect as though caused by the foreshortening of the leaf midrib. The arching effect is very severe and the curling may be described as "spiraled", the spiraling effect or curvature usually being through 180° to 340°. The shape, if laying on a flat plane, would be near ovate-acuminate with bi-lobes on each side of the midrib.

*Leaf size.*—Medium. 2½ to 5 inches long, measured along the midrib, and about 4 to 6 inches wide.

*Leaf petiole.*—Short and heavy. Color: Upper side — Near RHS 147A. Under side — Near RHS 147B.

*Retention.*—Good, but not as long lasting as the Hegg type of poinsettia.

Bracts: The bracts are many in number and form a round cushion-like appearance with a usual diameter of from 4½ to about 5½ inches. Tips of the bracts form a counterclockwise swirl when looking directly into the flowers of the plant, which are completely visible in this cultivar whereas on Ecke's Flaming Sphere, they are difficult to see.

*Size.*—Bracts are usually in the range of about 2 to 3½ inches long.

*Shape.*—Because of the shape of the bracts, it is difficult to describe; however, the photographic drawing best shows this feature.

*Petioles.*—The petioles are short and heavy and are not visible from the top.

*Color.*—Upper side — Near RHS 160C. Under side — Nearly the same as the upper side but the veins on the under side show a light green tinge.

*Ribs and veins.*—The ribs and veins are only slightly visible on top of the bracts but on the under side, they are of a light green tinge which provides a small contrast with the bract color.

*Retention.*—Good. The bracts last longer than the leaves.

As before mentioned, this poinsettia was produced as a hybrid by crossings of various seedlings or mutations, including the variety Ecke's Flaming Sphere (U.S. Plant Pat. No. 1,052), the other seedlings or mutations being unidentified. The unique characteristic of this cultivar is the shape or form of the individual leaves and bracts. In this respect, the leaves appear that they have been shortened by pulling a drawstring inside the midrib thus causing the leaves to pucker and curl.

I claim:

1. A new and distinctive white curly poinsettia plant, substantially as herein shown and described, distinguished by the puckered and severely arching effect of its leaves and bracts, and by its abundant and closely centered bracts which have an overall yellowish white color.

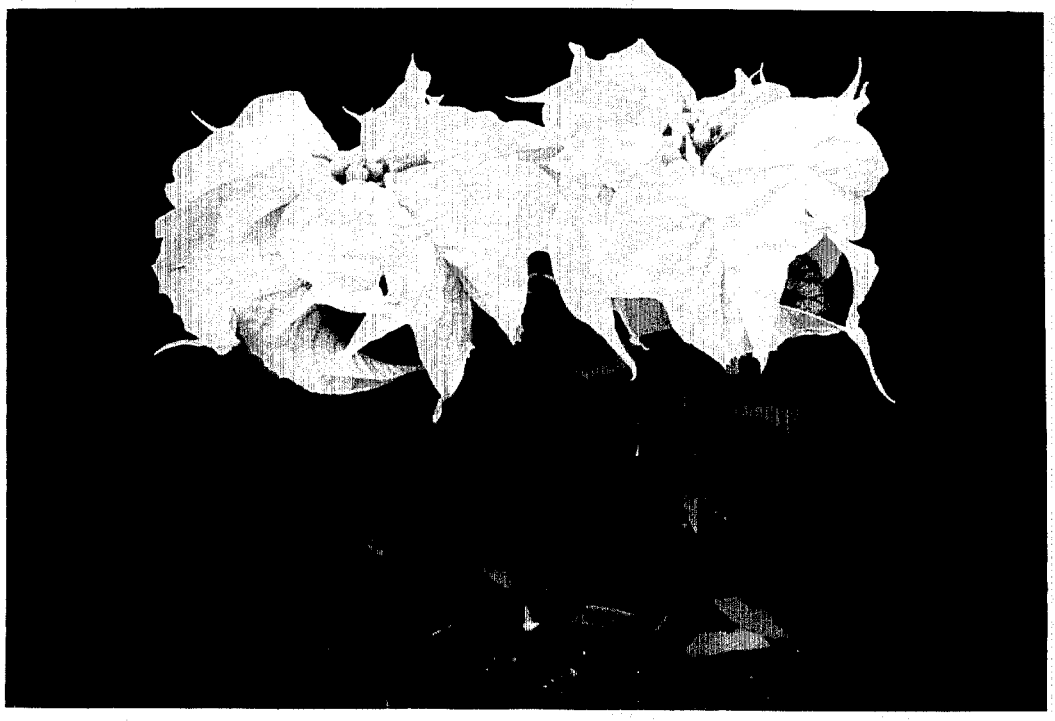
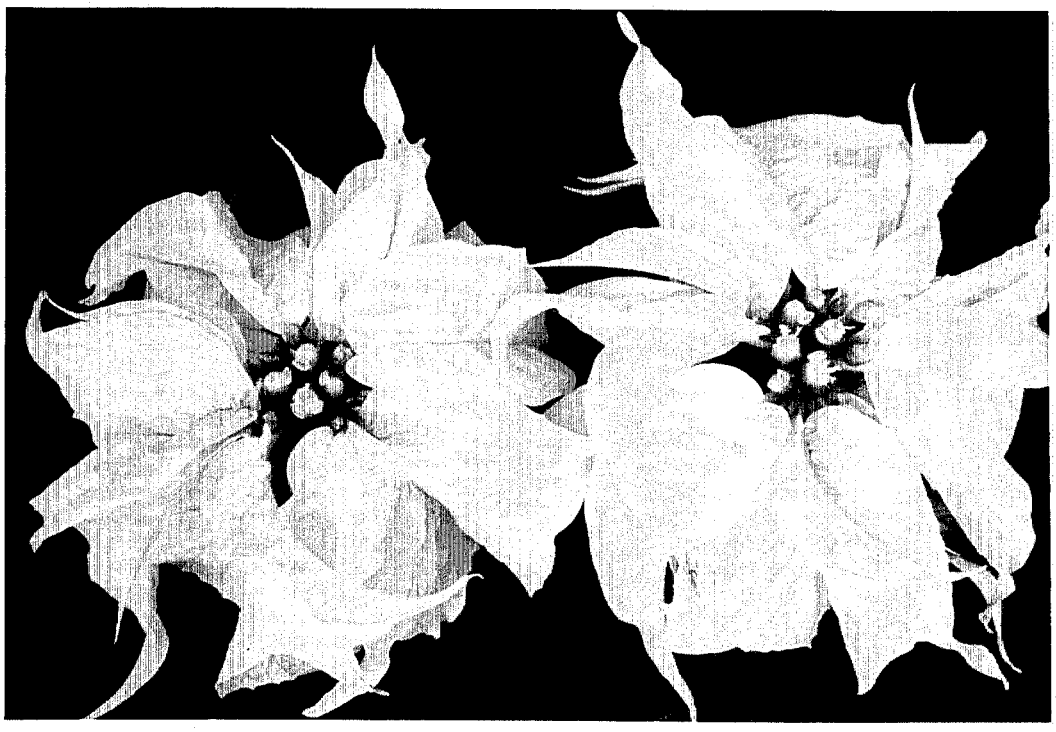

* * * * *